United States Patent
Dubovoy et al.

(10) Patent No.: US 10,206,858 B2
(45) Date of Patent: Feb. 19, 2019

(54) ALUMINUM CHLOROHYDRATE SALTS EXHIBITING HIGH SEC PEAK 1

(71) Applicant: Colgate-Palmolive Company, New York, NY (US)

(72) Inventors: Viktor Dubovoy, Cresskill, NJ (US); Long Pan, Somerset, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 15/512,966

(22) PCT Filed: Sep. 26, 2014

(86) PCT No.: PCT/US2014/057634
§ 371 (c)(1),
(2) Date: Mar. 21, 2017

(87) PCT Pub. No.: WO2016/048340
PCT Pub. Date: Mar. 31, 2016

(65) Prior Publication Data
US 2017/0246091 A1    Aug. 31, 2017

(51) Int. Cl.
| | |
|---|---|
| *A61K 8/26* | (2006.01) |
| *A61K 8/44* | (2006.01) |
| *A61Q 11/00* | (2006.01) |
| *A61Q 15/00* | (2006.01) |
| *C01F 7/56* | (2006.01) |
| *C01G 25/00* | (2006.01) |
| *C02F 1/52* | (2006.01) |

(52) U.S. Cl.
CPC .............. *A61K 8/26* (2013.01); *A61K 8/44* (2013.01); *A61Q 11/00* (2013.01); *A61Q 15/00* (2013.01); *C01F 7/56* (2013.01); *C01G 25/006* (2013.01); *C02F 1/5245* (2013.01); *A61K 2800/92* (2013.01); *C01P 2004/60* (2013.01); *C01P 2006/90* (2013.01)

(58) Field of Classification Search
None
See application file for complete search history.

(56) References Cited

U.S. PATENT DOCUMENTS

| | | | |
|---|---|---|---|
| 5,114,705 A | 5/1992 | Callaghan et al. | |
| 5,296,623 A * | 3/1994 | Katsoulis | A61K 8/26 |
| | | | 424/66 |
| 5,595,729 A | 1/1997 | Barr et al. | |
| 5,955,064 A | 9/1999 | Giovanniello et al. | |
| 6,066,314 A | 5/2000 | Tang et al. | |
| 6,074,632 A | 6/2000 | Shen et al. | |
| 6,342,210 B1 | 1/2002 | Cai et al. | |
| 7,704,531 B2 | 4/2010 | Tang et al. | |
| 8,257,689 B2 | 9/2012 | Pan et al. | |
| 8,562,956 B2 | 10/2013 | Pan et al. | |
| 2004/0022750 A1 * | 2/2004 | Lee | A61K 8/28 |
| | | | 424/66 |
| 2007/0110687 A1 | 5/2007 | Mattai et al. | |
| 2008/0233067 A1 | 9/2008 | Lee et al. | |
| 2011/0293532 A1 | 12/2011 | Babenko et al. | |
| 2014/0017189 A1 | 1/2014 | Pan | |
| 2015/0132242 A1 | 5/2015 | Yuan et al. | |

FOREIGN PATENT DOCUMENTS

| | | | |
|---|---|---|---|
| EP | 0444564 | 9/1991 | |
| WO | WO 1998/058626 | 12/1998 | |
| WO | WO 2001/097768 | 12/2001 | |
| WO | WO-2012148480 A1 * | 11/2012 | A61K 8/26 |
| WO | WO 2013/158077 | 10/2013 | |

OTHER PUBLICATIONS

International Search Report and Written Opinion in International Application No. PCT/US2014/057634, dated May 28, 2015.
Laden, ed., 1999, Ch. 3 "Axillary odor determination, formation, and control," and Ch. 4 "Chemistry of aluminum cholorhydrate and activated aluminum chlorohydrates," Antiperspirants and Deodorants, Marcel Dekker, Inc. pp. 59-136.

* cited by examiner

*Primary Examiner* — Michael P Cohen

(57) ABSTRACT

Aluminum chlorohydrate salts having an amount of Peak 1 material relative based on a total of Peaks 3, 4, and 5 of at least 20% as measured by size exclusion chromatography, together with water treatment compositions, antiperspirant compositions, and oral care compositions, comprising the same, and methods for making and using the same.

13 Claims, No Drawings

ALUMINUM CHLOROHYDRATE SALTS EXHIBITING HIGH SEC PEAK 1

BACKGROUND

Aluminium chlorohydrate is an aluminium salt formed from aluminum or aluminum hydroxide, hydrochloric acid, and water, and optionally also including zirconium and/or complexing agents such as amino acids or polyols. Such salts are used in deodorants and antiperspirants, and as coagulants or flocculants in water purification processes. In aqueous solution, these salts form complex substructures, e.g., $Al_{13}$ units with a Keggin ion structure, which in turn form larger polymeric species with molecular weights (MW) of over 1000 Daltons. The precise ratios of elements in these salts and the precise three dimensional structures formed can be controlled by method of manufacture. Typically, aluminum chlorohydrate salts may have the general formula $Al_nCl_{(3n-m)}(OH)_m$, e.g., $Al_2Cl(OH)_5$ or $Al_4Cl_2(OH)_{10}$. These salts may additionally be in complex with zirconium and/or an amino acid, ammonium acid, or a polyol, e.g., Al/Zr tetrachlorohydrex-Gly ($[Al_4Cl_2(OH)_{10}$ $ZrOCl_2]$ $NH_2CH_2COOH$).

Size exclusion chromatography ("SEC") or gel permeation chromatography ("GPC") provides information on polymer distribution of aluminum chlorohydrate in aqueous solutions. Distinctive peaks have been identified, corresponding to different size populations of the polymer complexes in solution, appearing in a chromatogram as peaks 1, 2, 3, 4 and a peak known as "5,6". Peak 1 is the larger species (greater than 60 Angstroms), generally observed only in salts with zirconium. Peaks 2 and 3 are larger aluminum species. Peak 4 is a smaller aluminum species (aluminum oligomers or small aluminum cluster). Peak 5, 6 is the smallest aluminum species.

There remains a need for aluminum chlorohydrate salts exhibiting a high SEC Peak 1.

BRIEF SUMMARY

Provided herein are aluminum chlorohydrate salts having an amount of Peak 1 material relative based on a total of Peaks 3, 4, and 5 of at least 20%, as measured by size exclusion chromatography. Methods of making these aluminum chlorohydrate salts are described. Methods of using these aluminum chlorohydrate salts in antiperspirants, oral care products, and water treatment compositions are also described.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The present disclosure is directed to aluminum chlorohydrate salts having a high SEC percentage of Peak 1. In some embodiments, these aluminum chlorohydrate salts are substantially free of zirconium, That is, the aluminum chlorohydrate salts of the disclosure comprise less than 5 weight percent of zirconium, preferably less than 4 weight percent, less than 3 weight percent, less than 2 weight percent, or less than 1 weight percent of zirconium.

Other embodiments of the disclosure, the aluminum chlorohydrate salts further comprise zirconium. Exemplary forms of zirconium include $ZrOCl_2.8H_2O$ and oxo-hexameric zirconium-octaamino acid.

The present disclosure is directed to aluminum chlorohydrate salts having an amount of Peak 1 material relative based on a total of Peaks 3, 4, and 5 of at least 20%, as measured by size exclusion chromatography. Preferably, the aluminum chlorohydrate salts of the disclosure have an amount of Peak 1 material relative based on a total of Peaks 3, 4, and 5 of at least 20, 30, 40. 50, 60, 70, 80, 90, 100, 112, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500%, as measured by size exclusion chromatography.

In preferred embodiments, the aluminum chlorohydrate salts of the disclosure exhibit a Peak 1.:Peak 4 ratio of at least 1:1.4. In other embodiments, the aluminum chlorohydrate salts of the disclosure exhibit a Peak 1:Peak 4 ratio of about 1:1.3, 1:1.2, 1:1.1; 1.1:1, 1.2:1, 1.3:1, 1.4:1, 1.5:1, 1.6:1, 1,7:1, 1.8:1, 1.9:1, 21:1, 2,2:1, 2.3:1, 2.4:1, 2,5:1, 2.6:1, 2.7:1, 2.8:1, 2,9:1, 3:1, 3.1:1, 3.2:1, 3.3:1, 3.4:1, 3.5:1, 3.6:1, 3.7:1, 3.8:1, 3.9:1, 4:1, 4.5:1, 5:1, 5.5:1, 6:1, 6.5:1, 7:1, 7.5:1, 8:1, 8.5:1, 9:1, 9.5:1, 10:1, 10.5:1, 11:1, 11.5:1, 12:1, 12.5:1, 13:1, 13.5:1, 14:1, 14.5:1, 15:1, 15,5:1, 16:1, 16,5:1, 17:1, 17.5:1, 18:1, 18.5:1, 19:1, 19.5:1, or 20:1.

In preferred embodiments, the aluminum chlorohydrate salts of the disclosure exhibit a Peak 1.:Peak 3 ratio of at least 1:1.4. In other embodiments, the aluminum chlorohydrate salts of the disclosure exhibit a Peak 1:Peak 3 ratio of at least 1:1.3, 1:1.2., 1:1.1; 1.1:1, 1.2:1, 1.3:1, 1.4:1, 1.5:1, 1.6:1, 1.7:1, 1.8:1, 1.9:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.5:1, 5:1, 5.5:1, 6:1, 6.5:1, 7:1, 7.5:1, 8:1, 8.5:1, 9:1, 9.5:1, 10:1, 10.5:1, 11:1, 11.5:1, 12:1, 12.5:1, 13:1, 13,5:1, 14:1, 14.5:1, 15:1, 15.5:1, 16:1, 16.5:1, 17:1, 117.5:1, 18:1, 18.5:1, 19:1, 19.5:11, 20:1, 20.5:1, 21:1, 21.5:1, 22:1, 22.5:1, 23:1, 23.5:1, 24:1, 24.5:1, or 25:1.

In preferred embodiments, the aluminum chlorohydrate salts of the disclosure exhibit a Peak 1:Peak 5 ratio of at least 1:2. In other embodiments, the aluminum chlorohydrate salts of the disclosure exhibit a Peak 1:Peak 5 ratio of about 1:1.9, 1:1.8, 1:1.7, 1:1.6, 1:1.5, 1:1.4, 1:1.3, 1:1.2, 1:1.1; 1.11:1, 1.2:1, 1.3:1, 1.4:11, 1.5:1, 1.6:1, 1.7:1, 11.8:1, 1.9:11, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.5:1, 5:1, 5.5:1, 6:1, 6.5:1, 7:1, 7.5:1, 8:11, 8.5:1, 9:1, 9.5:1, 10:1, 110.5:1, 11:1, 11.5:1, 112:11, 12.5:1, 13:1, 13.5:1, 14:1, 14.5:1, 15:1, 15.5:1, 16:1, 16.5:1, 17:1, 17,5:1, 18:1, 18.5:1, 19:1, 19.5:1, or 20:1.

In preferred embodiments, the aluminum chlorohydrate salts of the disclosure exhibit a Peak 1:(Peak 3+Peak 4) ratio of at least 1:3. Preferably, the aluminum chlorohydrate salts of the disclosure exhibit a Peak 1:(Peak 3+Peak 4) ratio of at least 1:2.9, 1:2.8, 1:2.7, 1:2.6, 1:2.5, 1:2.4, 1:2.3, 1:2.2, 1:2,1, 1.:2.0, 1:1.9, 1:1.8, 1:1,7, 1:1.6, 1:1.5, 1:1.4, 1:1,3, 1:1.2, 1:1.1, 1:1, 1.11:1, 1.2:1, 1.3:1, 1.4:1, 1.5:1, 11.6:1, 1.7:1, 1.8:11, 1.9:1, 2:1, 2.1:1, 2.2:1, 2.3:11, 2.4:1, 2.5:1, 2.6:1, 2.7:1, 2.8:1, 2.9:1, 3:1, 3.5:1, 4:1, 4.5:1, 5:1, 5,5:1, 6:1, 6.5:1, 7:1, 7.5:1, 8:1, 8.5:1, 9:1, 9.5:1, 10:1, 10.5:1, 11:1, 11.5:1, 12:1, 12.5:1, 13:1, 13.5:1, 14:1, 14.5:1, 15:1, 15.5:1, 16:1, 16.5:1, 17:1, 17.5:1, 18:1, 18.5:1, 19:1, 19.5:1, 20:1, 20.5:1, 21:1, 21,5:1, 22:1, 22.5:1, 23:1, 23.5:1, 24:1, 24.5:1, or 25:1.

Some embodiments of the disclosure include aluminum chlorohydrate salts having an amount of Peak 1 material relative based on a total of Peaks 1, 2, 3, 4, and 5 of at least 17%, as measured by size exclusion chromatography. Preferably, the aluminum chlorohydrate salts have an amount of Peak 1 material relative based on a total of Peaks 1, 2, 3, 4, and 5 of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81,82, 83, 84, 85, 86, 87, 88, 89, 90,91, 92, 93, 94, 95, 96, 97, 98, 99, or 100%, as measured by size exclusion chromatography.

The relative peak values may be determined using size exclusion chromatography (SEC). The relative retention time ("Kd") for each of the peaks varies depending on the experimental conditions, but the peaks remain relative to each other. Data for Tables in the examples is obtained using an SEC chromatogram using the following parameters: Waters®600 analytical pump and controller, Rheodyne® 7725I injector, Protein-Pak® 125 (Waters) column, Waters 2414 Refractive Index Detector. 0.1% potassium nitrate (w/v) with 0.055% nitric acid (w/v) mobile phase, 1 ml/min flow rate, 2.0 microliter injection volume. Data is analyzed using Water® Empower software (Waters Corporation, Milford, Mass.). The concentration of the aluminum salt in solution does not affect the retention time in the instrument.

The design of modern antiperspirant salts generally aims at actives with high levels of low molecular weight Al and Zr species, which is reflected in a SEC chromatogram that has intense Peak 4 and low Peaks 1, 2, and 3, in contrast to the present disclosure which aims at compositions having relatively high Peak 1 content and no zirconium.

Throughout the present study, the relative concentration of Peaks 1-5 are estimated based on the following SEC peak area ratios (or percentages):

$$f_{Pi} = \frac{Pi}{\Sigma Pj} \quad i = 1, 2, 3, 4, 5; \, j = 2, 3, 4, 5$$

where fPi is the fraction of peak i, and Pi or Pj represent the intensity of peaks Pi or Pj, respectively, intensity generally correlating with area under the curve or amount of material. In brief, a preferred aluminum chlorohydrate salt would have a very low fP3, fP4, and/or fP5, and a high fP1.

A variety of hydrolytic Al species exist and it is possible to distinguish large aqueous aluminum hydroxide molecules using spectroscopic methods such as $^{27}$Al NMR which elucidates the structural environment surrounding Al atoms which are embodied in various forms. There are typically two regions in a $^{27}$Al NMR spectrum, one of Al nuclei that are octahedrally coordinated (0 ppm-60 ppm) and the other of Al nuclei that are tetrahedrally coordinated (60 ppm-85 ppm). The octahedral region is exemplified by the hexa-aqua Al species, i.e. monomeric Al, which resonates sharply near 0 ppm. The tetrahedral region is exemplified by resonance near 63.5 ppm from the $Al_{13}$ polyhydroxyoxoaluminum cation. $Al_{13}$ is composed of 12 octahedrally coordinated Al atoms surrounded by one centrally-cited Al atom which is tetrahedrally coordinated. The $Al_{30}$ polyhydroxyoxoaluminum cation is essentially a dimer of the $Al_{13}$ polyhydroxyoxoaluminum cation and contains 2 tetrahedrally sited Al atoms which yield a somewhat broad resonance near 70 ppm. Depending on calibration, the above ppm values can vary, The values for these peaks are approximately where the resonance occurs.

Peak 1 of the aluminum chlorohydrate, salts of the disclosure is found to be predominantly made up of octohedrally coordinated aluminum.

The compositions may be made in a variety of ways using a water-soluble zwitterionic compound with an isoelectric point above 7 and/or a water-soluble organic compound with a pKa of greater than 7. The procedure generally includes the step of heating an aqueous solution containing an aluminum chloride compound and a water-soluble zwitterionic compound with an isoelectric point above 7 and/or a water-soluble organic compound with a pKa of greater than 7, preferably an amino acid such as basic amino acid, at a temperature of 40° C. to 95° C. to reflux for a period of time of about 1 hour to about 5 hours, or to about 1 day, or to about 3 days, or to about 5 days. In one embodiment, the temperature is 45° C. to 75° C. In another embodiment, the temperature is 45° C. to 55° C. In one embodiment, the temperature is about 50° C.

According to the disclosure, the water-soluble zwitterionic compound with an isoelectric point above 7 and/or the water-soluble organic compound with a pKa of greater than 7 is an amino acid. Preferably, the amino acid is a basic amino acid, for example, arginine, lysine, and/or histidine. An exemplary amino acid is arginine, preferably L-arginine. In some embodiments, the water-soluble zwitterionic compound with an isoelectric point above 7 and/or the water-soluble organic compound with a pKa of greater than 7 to aluminum molar ratio is 2.25:1 to 3:1. In another such embodiment, the water-soluble zwitterionic compound with an isoelectric point above 7 and/or the water-soluble organic compound with a pKa of greater than 7 to aluminum molar ratio is 2.5:1 to 3:1. In another such embodiment, the water-soluble zwitterionic compound with an isoelectric point above 7 and/or the water-soluble organic compound with a pKa of greater than 7 to aluminum molar ratio is 2.5:1 to 2.75:1. In another such embodiment, the water-soluble zwitterionic compound with an isoelectric point above 7 and/or the water-soluble organic compound with a pKa of greater than 7 to aluminum molar ratio is 2.75:1 to 3:1. In another such embodiment, the water-soluble zwitterionic compound with an isoelectric point above 7 and/or the water-soluble organic compound with a pKa of greater than 7 to aluminum molar ratio is about 2.75:1.

In some embodiments, the amino acid to aluminum molar ratio is 2.25:1 to 3:1. In another such embodiment, the amino acid to aluminum molar ratio is 2.5:1 to 3:1. In another such embodiment, the amino acid to aluminum molar ratio is 2.5:1 to 2.75:1. In another such embodiment, the amino acid to aluminum molar ratio is 2.75:1 to 3:1, 1111 another such embodiment, the amino acid to aluminum molar ratio is about 2.75:1.

In exemplary embodiments, the arginine to aluminum molar ratio is 2.25:1 to 3:1. In another such embodiment, the arginine to aluminum molar ratio is 2.5:1 to 3:1. In another such embodiment, the arginine to aluminum molar ratio is 2.5:1 to 2.75:1. In another such embodiment, the arginine to aluminum molar ratio is 2.75:1 to 3:1. In another such embodiment, the arginine to aluminum molar ratio is about 2.75:1.

For the above methods, the aluminum chloride salt may be obtained from a variety of sources. In one embodiment, the aluminum chloride salt includes aluminum trichloride, aluminum chlorohexahydrate and aluminum dichlorohydrate. In one such embodiment, the aluminum chloride salt is aluminum chlorohexahydrate.

The polymerization of the aluminum chloride actives in aqueous solutions and the correspondent gelation process are followed by monitoring the molecular weight profile of the polyoxohalides in time by SEC. The relative retention time ("Kd") for each of these peaks varies depending on the experimental conditions, but the peaks remain relative to each other. The concentration of the aluminum chloride in solution does not affect the retention time in the machine.

The present disclosure thus provides for methods of making aluminum chlorohydrate salts having an amount of Peak 1 material relative based on a total of Peaks 3, 4, and 5 is at least 20% as measured by size exclusion chromatography, comprising heating an initial ACH solution at a temperature of 40-95° C., e.g. 45-55° C., e.g., about 50° C., in presence of an amino acid, preferably a basic amino acid, e.g., arginine, until Peak 1 material becomes one of the dominant species, preferably the dominant species.

In some embodiments, the aluminum chloride salts are made from a salt as described in 21 CFR 350.10, e.g., a salt which meets the aluminum to chloride atomic ratios described in the U.S. Pharmacopeia-National Formulary. Exemplary aluminum chlorohydrates and complexes thereof include:

Aluminum chloride,
Aluminum chlorohydrate.
Aluminum dichlorohydrate.
Aluminum sesquichlorohydrate.
Aluminum zirconium octachlorohydrate.
Aluminum zirconium pentachlorohydrate.
Aluminum zirconium tetrachlorohydrate. Aluminum zirconium trichlorohydrate.

Water Treatment:

In one embodiment, the disclosure provides compositions for water treatment, e.g., as a flocculant or coagulant, comprising an aluminum chlorohydrate salt of the disclosure.

The disclosure thus provides a method of removing solids from water, e.g., reducing turbidity or cloudiness of water, comprising adding to the water an aluminum chlorohydrate salt of the disclosure, and removing the gel thus formed from the water.

Antiperspirant:

In another embodiment, the disclosure provides an antiperspirant composition comprising an aluminum chlorohydrate salt of the disclosure.

The aluminum antiperspirant active compositions may be used in a variety of antiperspirant products. If the product is used as a solid powder, the size of the particles of antiperspirant active of the disclosure can be any desired size, and may include conventional sizes such as in the range of 2 to 100 microns, with selected grades having an average particle size of 30-40 microns; finer sized grades having an average particle size distribution of 2-10 microns with an average size of about 7 microns as made by a suitable dry-grinding method; and micronized grades having an average particle size of less than about or equal to 2 microns, or less than about or equal to 1.5 microns.

The compositions of this disclosure may be used to formulate antiperspirants which are tolerated by consumers having sensitive skin. Such antiperspirants include solids such as sticks and creams (creams sometimes being included in the term "soft solid"), gels, liquids (such as are suitable for roll-on products), and aerosols. The forms of these products may be suspensions or emulsions. These antiperspirant actives can be used as the antiperspirant active in any antiperspirant composition.

Note that where water is listed it is intended to count the contribution of the water present in the antiperspirant solution as part of the overall water content. Thus, water is sometimes listed as part of the actives solution or sometimes listed separately.

In one embodiment the refractive indices of the external and internal phases are matched within 0.005 to obtain a clear product.

Antiperspirant compositions can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skirt. For sticks, sprays, aerosols and roll-cans the compositions can be placed in a conventional types of container (with the inclusion of propellants in aerosols). This provides good deposition of the active material on the skin.

Compositions can be formulated as clear, translucent or opaque products. A desired feature of the present disclosure is that a clear, or transparent, cosmetic composition, (for example, a clear or transparent deodorant or antiperspirant composition) can be provided. The term clear or transparent according to the present disclosure is intended to connote its usual dictionary definition; thus, a clear liquid or gel antiperspirant composition of the present disclosure allows ready viewing of objects behind it. By contrast, a translucent composition, although allowing light to pass through, causes the light to be scattered so that it will be impossible to see clearly objects behind the translucent composition. An opaque composition does not allow light to pass there through. Within the context of the present disclosure, a gel or stick is deemed to be transparent or clear if the maximum transmittance of light of any wavelength in the range 400-800 nm through a sample 1 cm thick is at least 35%, or at least 50%. The gel or liquid is deemed translucent if the maximum transmittance of such light through the sample is between 2% and less than about 35%. A gel or liquid is deemed opaque if the maximum transmittance of light is less than about 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334 A2. Thus, according to the present disclosure, there are differences between transparent (clear), translucent and opaque compositions.

Oral Care:

Dentinal hypersensitivity is acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity. Dentinal tubules open to the surface have a high correlation with dentine hypersensitivity. Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients. The particles of the aluminum chlorohydrate of the disclosure are surprisingly found to be of a size and charge which is effective in blocking and adhering to the dentinal tubules, thereby reducing this fluid flow and reducing the sensitivity of hypersensitive teeth.

In one embodiment, the disclosure provides an oral care product, e.g., a dentifrice, comprising an aluminum chlorohydrate salt of the disclosure.

In another embodiment, the oral care products further comprise an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof, for example, comprising an effective amount of sodium monofluorophosphate.

In another embodiment, the oral care products further comprise an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca, 5%, by weight of the composition.

In another embodiment, the oral care products further comprise buffering agents, e.g., sodium phosphate buffer (e.g., sodium phosphate monobasic and disodium phosphate).

In another embodiment, the oral care products further comprise a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.

In another embodiment, the oral care products further comprise one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine.

In another embodiment, the oral care products further comprise comprising a viscosity modifying amount of one or more of polysaccharide gums, for example xanthan gum or carrageenan, silica thickener, and combinations thereof.

In another embodiment, the oral care products further comprise comprising gum strips or fragments.

In another embodiment, the oral care products further comprise flavoring, fragrance and/or coloring.

In another embodiment, the oral care products further comprise an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide domiphen bromide, delmopinol, octapinol and other piperidino derivatives, nicin preparations, chlorite salts; and mixtures of any of the foregoing; e.g., comprising triclosan or cetylpyridinium chloride.

In another embodiment, the oral care products further comprise an antibacterially effective amount of triclosan, e.g. 0.1-0.5%, e.g. about 0.3%.

In another embodiment, the oral care products further comprise a whitening agent, e.g., a selected from the group consisting of peroxides, metal chlorites, perborates, percarbonates, peroxyacids, hypochlorites, and combinations thereof.

In another embodiment, the oral care products further comprise hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

In another embodiment, the oral care products further comprise an agent that interferes with or prevents bacterial attachment, e.g., solbrol or chitosan.

In another embodiment, the oral care products further comprise a source of calcium and phosphate selected from (i) calcium-glass complexes, e.g., calcium sodium phosphosilicates, and (ii) calcium-protein complexes, e.g., casein phosphopeptide-amorphous calcium phosphate In another embodiment, the oral care products further comprise a soluble calcium salt, e.g., selected from calcium sulfate, calcium chloride, calcium nitrate, calcium acetate, calcium lactate, and combinations thereof.

In another embodiment, the oral care products further comprise a physiologically or orally acceptable potassium salt, e.g., potassium nitrate or potassium chloride, in an amount effective to reduce dentinal sensitivity.

In another embodiment, the oral care products further comprise an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g. wherein the anionic polymer is about 1-5%, e.g., about 2%, of the weight of the composition.

In another embodiment, the oral care products further comprise a breath freshener, fragrance or flavoring.

The pH of the oral care products of the disclosure is approximately neutral, e.g., from pH 6 to pH 8 e.g., about pH 7.

In one embodiment, the oral care products of the disclosure are for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

Also provided herein are methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of an oral care product of the disclosure to the teeth. The disclosure further provides oral care products of the disclosure for use in any of these methods.

Also provided herein is the use of an aluminum chlorohydrate salt having an amount of Peak 3 material relative based on a total of Peaks 3, 4, and 5 is at least 20% as measured by size exclusion chromatography in the manufacture of an oral care product to reduce and inhibit acid erosion of the enamel, clean the teeth, reduce bacterially-generated biofilm and plaque, reduce gingivitis, inhibit tooth decay and formation of cavities, and reduce dentinal hypersensitivity.

EXAMPLES

Example 1

L-Arginine was combined with aluminum chloride hexaaqua solution (1.4% aluminum) at arginine:aluminum molar ratios of 0:1, 1.:1, 1,25:1, 1,5:1, 1.75:1. 2:1, 2,25:1, 2.5:1. 2.75:1, and 3:1. The mixtures were aged at 50° C. for 5 days. Visual assessment was conducted at 1, 3, and 5 days of ageing, to observe colloidal formation. pH measurements were performed at day 3. Turbidity measurements were made at day 5. Results are shown in Table 1.

TABLE 1

| Arg/Al (mol) | Arginine (g) | 1.5% Al Sol'n (g) | pH | Turbidity (% Trans) | Visual initial | 1 day | 3 day | 5 day |
|---|---|---|---|---|---|---|---|---|
| 0 | 0 | 10.0190 | 2.14 | 89.65 | PASS | PASS | PASS | PASS |
| 1 | 1.0103 | 10.0017 | 3.09 | 88.85 | PASS | PASS | PASS | PASS |
| 1.25 | 1.2633 | 9.9993 | 3.26 | 90.34 | PASS | PASS | PASS | PASS |
| 1.51 | 1.5165 | 10.0026 | 3.35 | 91.05 | PASS | PASS | PASS | PASS |
| 1.75 | 1.7674 | 10.0008 | 3.54 | 90.01 | PASS | PASS | PASS | PASS |
| 2.01 | 2.0204 | 10.0001 | 3.77 | 86.08 | PASS | FAIL | PASS | PASS |
| 2.26 | 2.2728 | 10.0000 | 3.81 | 78.94 | PASS | FAIL | FAIL | FAIL |
| 2.51 | 2.5244 | 9.9980 | 4.01 | 86.55 | FAIL | FAIL | PASS | PASS |
| 2.76 | 2.7779 | 10.0014 | 4.40 | 89.43 | FAIL | PASS | PASS | PASS |
| 3.01 | 3.0298 | 9.9973 | 6.92 | 89.17 | FAIL | PASS | PASS | PASS |

Size exclusion chromatography was performed on each sample. The results are shown in Table 2.

TABLE 2

| Arg/Al | SEC Peak Areas (%) | | | |
|---|---|---|---|---|
| (mol) | Peak 1 | Peak 3 | Peak 4 | Peak 5 |
| 0 | 0 | 0 | 0 | 100 |
| 1 | 0 | 0.92 | 3.06 | 96.03 |

TABLE 2-continued

| Arg/Al | SEC Peak Areas (%) | | | |
|---|---|---|---|---|
| (mol) | Peak 1 | Peak 3 | Peak 4 | Peak 5 |
| 1.25 | 0.04 | 3.36 | 7.48 | 89.12 |
| 1.51 | 0.05 | 7.42 | 12.31 | 80.22 |
| 1.75 | 0 | 13.47 | 17.90 | 68.63 |
| 2.01 | 0.06 | 24.04 | 22.30 | 53.60 |
| 2.26 | 16.88 | 26.70 | 23.75 | 32.67 |
| 2.51 | 56.12 | 12.03 | 17.85 | 14.00 |
| 2.76 | 82.21 | 0 | 7.28 | 10.51 |
| 3.01 | 44.88 | 0 | 0 | 55.12 |

The $^{27}Al$ NMR spectrum of purified peak 1 solution shows a dominant, sharp OH—Al peak at 8 ppm and a small sharp peak at 2 ppm. This data suggests a presence of octahedral aluminum environments. Fourier transform IR (not shown) of freeze dried purified Peak 1 powder does not exhibit a carboxylate stretch, suggesting a lack of coordination of arginine functional groups to aluminum. Elemental analysis of purified solution and powder validates the absence of stoichiometric amounts of arginine.

What is claimed is:

1. An aluminum chlorohydrate salt composition having an area of Peak 1 material relative to the sum of the areas of Peaks 3, 4, and 5 of at least 20%, as measured by size exclusion chromatography, wherein the composition further comprises arginine, and the molar ratio of arginine:aluminum is 2.25:1 to 3:1.

2. The salt composition of claim 1, wherein the area of Peak 1 material relative to the sum of the areas of Peaks 3, 4, and 5 is at least 80%, as measured by size exclusion chromatography.

3. The salt composition of claim 1, wherein:
a Peak 1:Peak 4 ratio is at least 1:1.4,
a Peak 1:Peak 3 ratio is at least 1:1.5,
a Peak 1:Peak 5 ratio is at least 1:2, or
a Peak 1:Peak 3+Peak 4 ratio is at least 1:3.

4. The salt composition of claim 1, having an area of Peak 1 material relative to the sum of the areas of Peaks 1, 2, 3, 4, and 5 of at least 56%, as measured by size exclusion chromatography.

5. The salt composition of claim 1, wherein the salt is substantially free of zirconium.

6. The salt composition of claim 1, wherein the aluminum chlorohydrate further comprises zirconium, and wherein the zirconium is $ZrOCl_2.8H_2O$ or oxo-hexameric zirconium-octaamino acid.

7. A water treatment composition comprising the salt composition of claim 1.

8. An antiperspirant composition comprising the salt composition of claim 1 and an antiperspirant carrier.

9. An oral care product comprising the salt composition of claim 1 and an oral care carrier.

10. A method of making a salt, comprising heating an initial aluminum salt solution at a temperature of about 50°C., in the presence of arginine, until the area of Peak 1 material relative to the sum of the areas of Peaks 3, 4, and 5 is at least 20% as measured by size exclusion chromatography, wherein the aluminum salt is at least one of aluminum chloride, aluminum chlorohydrate, aluminum dichlorohydrate, aluminum sesquichlorohydrate, aluminum zirconium octachlorohydrate, aluminum zirconium pentachlorohydrate, aluminum zirconium tetrachlorohydrate, or aluminum zirconium trichlorohydrate, and wherein the molar ratio of arginine:aluminum is 2.25:1 to 3:1.

11. A method of treating water comprising adding the composition of claim 7 to water.

12. A method of reducing perspiration comprising applying the antiperspirant of claim 8 to skin.

13. A method of treating or reducing dental hypersensitivity and/or erosion comprising applying an effective amount of oral care product according to claim 9 to the teeth of a patient in need thereof.

* * * * *